United States Patent
Matsutani et al.

(10) Patent No.: US 11,676,271 B2
(45) Date of Patent: Jun. 13, 2023

(54) DYNAMIC IMAGE ANALYSIS APPARATUS EXTRACTING SPECIFIC FRAMES INCLUDING A DETECTION TARGET FROM A DYNAMIC IMAGE, DYNAMIC ANALYSIS SYSTEM, AND STORAGE MEDIUM

(71) Applicant: KONICA MINOLTA, INC., Tokyo (JP)

(72) Inventors: Noritsugu Matsutani, Musashino (JP); Sumiya Nagatsuka, Hino (JP); Yuki Kawana, Hino (JP)

(73) Assignee: KONICA MINOLTA, INC., Tokyo (JP)

( * ) Notice: Subject to any disclaimer, the term of this patent is extended or adjusted under 35 U.S.C. 154(b) by 243 days.

(21) Appl. No.: 17/082,926

(22) Filed: Oct. 28, 2020

(65) Prior Publication Data

US 2021/0133967 A1   May 6, 2021

(30) Foreign Application Priority Data

Nov. 1, 2019 (JP) .............................. JP2019-199844
Mar. 12, 2020 (JP) .............................. JP2020-042548
Mar. 23, 2020 (JP) .............................. JP2020-050422

(51) Int. Cl.
   *G06T 7/00* (2017.01)

(52) U.S. Cl.
   CPC .. *G06T 7/0012* (2013.01); *G06T 2207/10116* (2013.01)

(58) Field of Classification Search
   None
   See application file for complete search history.

(56) References Cited

U.S. PATENT DOCUMENTS 7,230,262 B2 * 6/2007 Sendai .................. G03B 42/08
                                                              250/583
7,269,246 B2    9/2007 Ohishi
(Continued)

FOREIGN PATENT DOCUMENTS

JP    H11151234 A    6/1999
JP    2004086802 A    3/2004
(Continued)

OTHER PUBLICATIONS

Japanese Office Action (and an English language translation thereof) dated Mar. 28, 2023, issued in counterpart Japanese Application No. 2019-199844.
(Continued)

*Primary Examiner* — Miya J Williams
*Assistant Examiner* — Pawan Dhingra
(74) *Attorney, Agent, or Firm* — Holtz, Holtz & Volek PC (57) ABSTRACT

A non-transitory computer-readable storage medium stores a program that causes a computer to perform an obtaining process, an analyzing process, and an extracting process. In the obtaining process, the computer obtains a radiographic moving image showing a motion of a specific part of an examinee. In the analyzing process, the computer analyzes the radiographic moving image obtained in the obtaining process. In the extracting process, the computer extracts, among frames constituting the radiographic moving image, a specific frame that visibly shows a detection target in the specific part, based on a result of analyzing a dynamic state of the specific part in the analyzing process.

16 Claims, 5 Drawing Sheets

(56) References Cited

U.S. PATENT DOCUMENTS

| | | | | |
|---|---|---|---|---|
| 10,262,419 B2* | 4/2019 | Tezuka | ................... | H04N 5/268 |
| 10,827,999 B2* | 11/2020 | Matsutani | .............. | A61B 6/507 |
| 2018/0018772 A1 | 1/2018 | Fujiwara et al. | | |
| 2019/0298287 A1* | 10/2019 | Nagatsuka | ........... | A61B 6/5205 |
| 2020/0005458 A1 | 1/2020 | Matsutani | | |
| 2020/0069967 A1 | 3/2020 | Mori et al. | | |

FOREIGN PATENT DOCUMENTS

| | | | |
|---|---|---|---|
| JP | 2007130244 A | 5/2007 | |
| JP | 2012147978 A | 8/2012 | |
| JP | 2018007801 A | 1/2018 | |
| JP | 2018075356 A | 5/2018 | |

OTHER PUBLICATIONS

Fudeya, et al., "Visualization of Laryngopharynx during Swallowing of Negative Contrast Media (Air) with Cine Mode 64-row MDCT", Japanese Society of Radiological Technology, 2010, vol. 66, 5th pp. 535-540.

* cited by examiner

DYNAMIC IMAGE ANALYSIS APPARATUS EXTRACTING SPECIFIC FRAMES INCLUDING A DETECTION TARGET FROM A DYNAMIC IMAGE, DYNAMIC ANALYSIS SYSTEM, AND STORAGE MEDIUM

CROSS-REFERENCE TO RELATED APPLICATIONS

The entire disclosure of Japanese Patent Application No. 2019-199844 filed on Nov. 1, 2019, No. 2020-042548 filed on Mar. 12, 2020, and No. 2020-050422 filed on Mar. 23, 2020 are incorporated herein by reference in its entirety.

BACKGROUND

Technological Field

The present disclosure relates to a computer-readable storage medium, a dynamic analysis apparatus, and a dynamic analysis system.

Description of the Related Art

Generating a plurality of radiographic images of a subject in different imaging directions has been performed by an imaging apparatus, such as an angiographic X-ray apparatus. More specifically, the subject is placed between an X-ray tube and an X-ray detector that can be rotated around the subject, and the apparatus images the subject multiple times while rotating the X-ray tube and the X-ray detector (for example, see JP2007-130244A).

On the other hand, radiographic images have been used to obtain information on specific detection targets, such as an incomplete fracture and a gap between bones, which occur in specific parts of a subject (e.g., bones and joints). The detection target may be visible only when imaged in a certain direction, but may not be shown on images when imaged in other directions.

The part including a detection target can be imaged in multiple directions by using the apparatus having a rotating mechanism disclosed in JP2007-130244A. However, a person who performs imaging may not capture images of the detection target or may spend long time to capture them, because the person has to determine imaging directions.

Further, a detection target in a specific part of a subject may be invisible regardless of imaging directions, owing to the state of the region (e.g., how much the joint is bended). Such detection target cannot be detected with the apparatus disclosed in JP2007-130244A, which captures images while rotating the X-ray tube and the X-ray detector.

SUMMARY

The present disclosure has been conceived in view of the above issues. Objects of the present disclosure include detecting, in specific parts, specific detection targets that are visible only when imaged under a certain condition more easily than the related art.

To achieve at least one of the abovementioned objects, according to an aspect of the present invention, there is provided a non-transitory computer-readable storage medium storing a program that causes a computer to perform:

an obtaining process of obtaining a radiographic moving image showing a motion of a specific part of an examinee;

an analyzing process of analyzing the radiographic moving image obtained in the obtaining process; and an extracting process of extracting, among frames constituting the radiographic moving image, a specific frame that visibly shows a detection target in the specific part, based on a result of analyzing a dynamic state in the analyzing process.

To achieve at least one of the abovementioned objects, according to another aspect of the present invention, there is provided a dynamic analysis apparatus including a hardware processor that:

obtains a radiographic moving image showing a specific part of an examinee;

analyzes the obtained radiographic moving image; and based on a result of the analysis, extracts, among frames constituting the radiographic moving image, a specific frame that visibly shows a detection target in the specific part.

To achieve at least one of the abovementioned objects, according to another aspect of the present invention, there is provided a dynamic analysis system, including:

a moving-image generator that generates a radiographic moving image showing a specific part of an examinee; and a hardware processor that:

analyzes the radiographic moving image generated by the moving-image generator; and based on a result of the analysis, extracts, among frames constituting the radiographic moving image, a specific frame that visibly shows a detection target in the specific part.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention, wherein.

DETAILED DESCRIPTION OF THE EMBODIMENTS

Hereinafter, one or more embodiments of the present invention are described with reference to the drawings. However, the scope of the invention is not limited to the disclosed embodiments and the drawings.

<1. Dynamic Analysis System>

Figure 1:
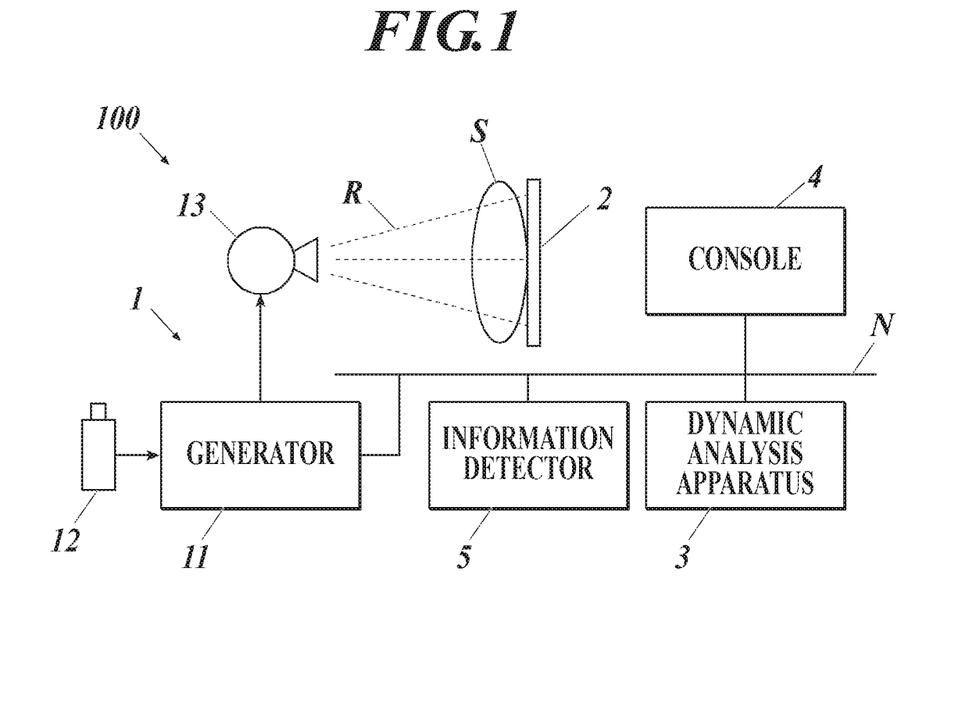
FIG. 1 is a block diagram showing a dynamic analysis system as an embodiment of the present invention.
Figure 2:
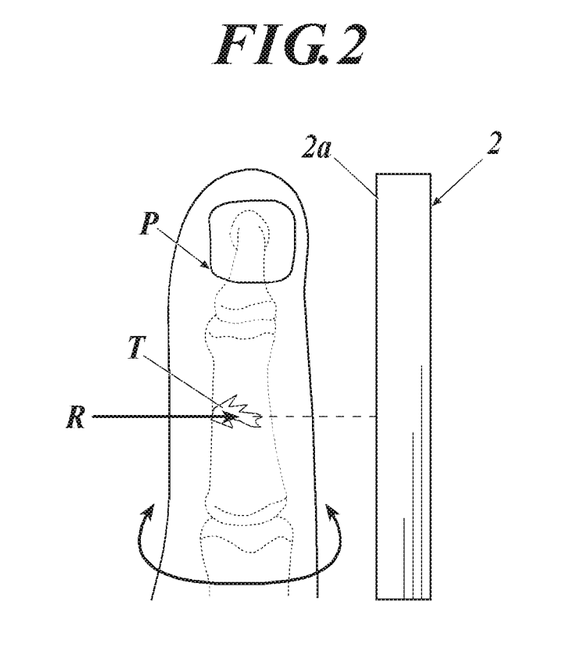
FIG. 2 shows an example of how to image a specific part.
Figure 3A:
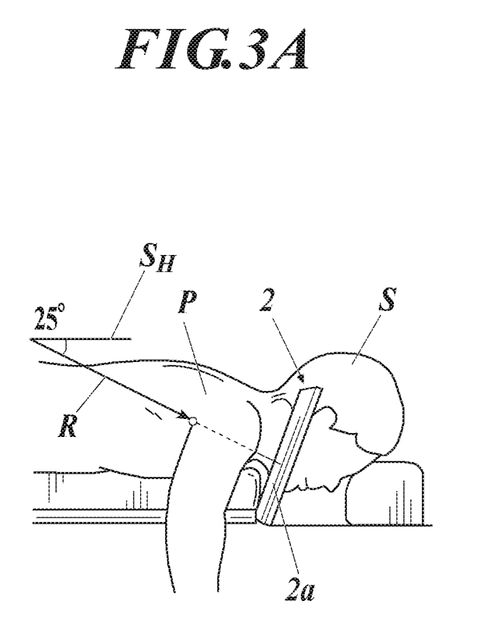
FIG. 3A shows an example of how to image a specific part.
Figure 3B:
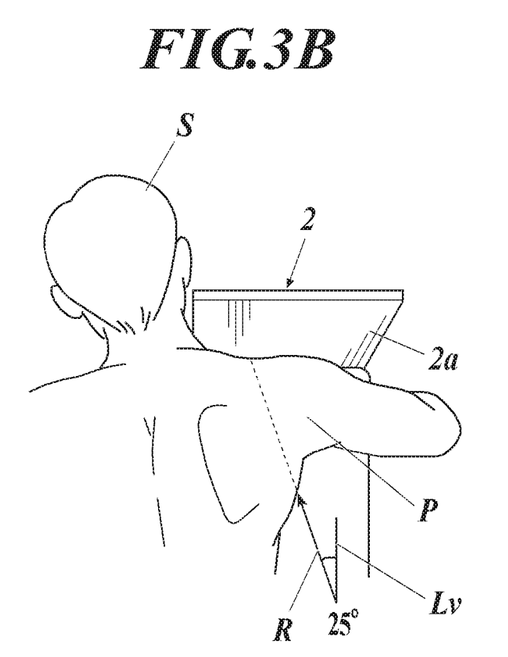
FIG. 3B shows an example of how to image a specific part.
Figure 4:
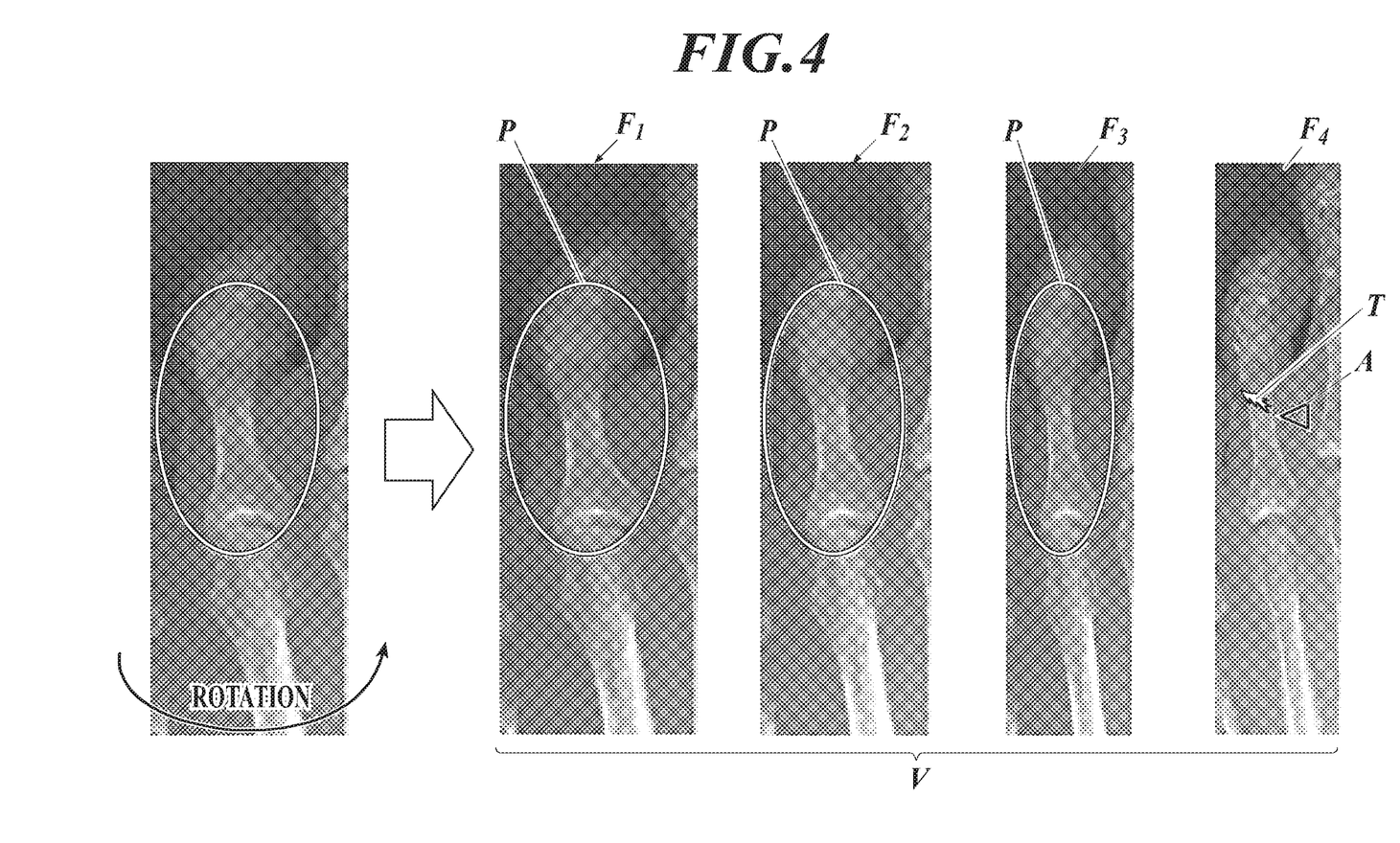
FIG. 4 shows an example of a radiographic moving image generated by the system in FIG. 1.
Figure 5:
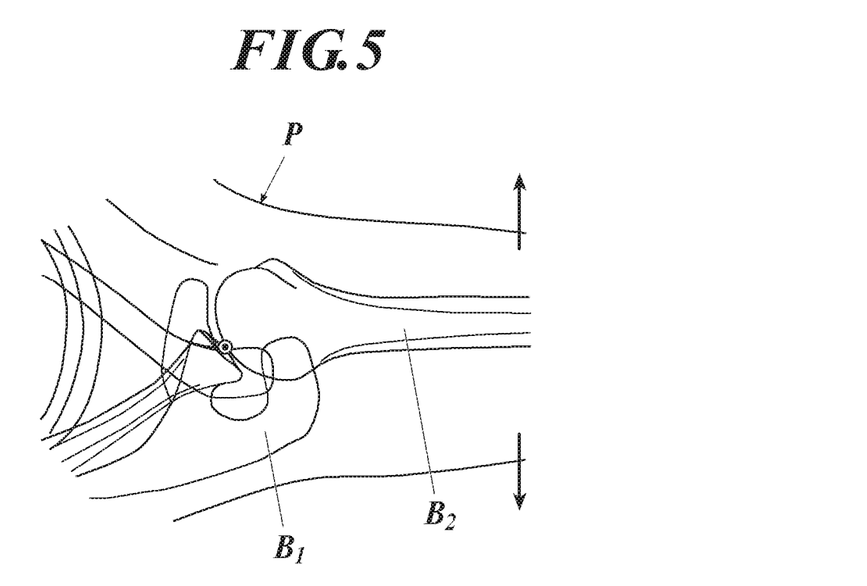
FIG. 5 shows another example of the radiographic moving image generated by the system in FIG. 1.

Firstly, a schematic configuration of a dynamic analysis system (hereinafter called system 100) according to this embodiment is described. FIG. 1 is a block diagram of the system 100. FIGS. 2, 3A, and 3B show examples of how to image a specific part P. FIGS. 4, 5 show examples of a radiographic moving image V generated by the system 100.

The system 100 includes a radiation generator 1, a radiation detector 2, and a dynamic analysis apparatus 3, as shown in FIG. 1.

The system 100 of this embodiment further includes a console 4.

The components 1 to 5 can communicate with one another over a communication network N, such as a Local Area Network (LAN), a Wide Area Network (WAN), or the Internet.

The system 100 may be capable of communicating with other systems, such as the hospital information systems (HIS), the radiology information systems (RIS), and the picture archiving and communication systems (PACS), which are not illustrated.

(Radiation Generator)

The radiation generator 1 includes a generator 11, an irradiation instruction switch 12, and a radiation source 13.

The radiation generator 1 may be installed in an imaging room or may constitute a movable instrument carriage along with the console 4 and other components.

When the irradiation instruction switch 12 is operated, the generator 11 applies a voltage to the radiation source 13 (tubular lamp) according to preset imaging conditions. Examples of the imaging conditions include: conditions concerning a subject S, such as parts to be imaged, imaging directions, and the physical characteristic of the subject S; and conditions concerning radiation R to be emitted, such as tube voltage, tube current, irradiation time, and current time product (mAs).

When the voltage is applied by the generator 11, the radiation source 13 generates radiation R (e.g., X-rays) having a dose corresponding to the applied voltage.

The radiation source 13 is movable in X-axis, Y-axis, and Z-axis directions that are orthogonal to each other. The radiation source 13 is also rotatable on axes parallel to Y-axis and Z-axis to change the direction of the irradiation hole.

The radiation generator 1 configured as described above generates radiation R according to the type of imaging, namely which is captured, a still image or a moving image.

The radiation generator 1 can also irradiate a certain part (e.g., bone or joint) of the subject S in a certain posture (e.g., standing, sitting, or laying) with radiation R such that the irradiation direction (direction of the optical axis of radial rays) forms certain angles with a horizontal plane SH and a vertical line Lv.

The radiation generator 1 thus serves as an irradiator.

(Radiation Detector)

The radiation detector 2 includes the following not-shown components: radiation detection elements that generate charges corresponding to the dose of radiation when irradiated with radiation R; a sensor substrate on which pixels are arranged two-dimensionally (in a matrix), the pixels having switch elements that accumulate/release charges; a scanning circuit that switches on/off of each switch element; a reading circuit that reads out an amount of charges released by each pixel as an signal; a controlling part that generates a radiographic image based on the signals read out by the reading circuit; and a communicating part that sends data of the generated radiographic image and various signals to the outside and receives various kinds of information and signals.

When irradiated with radiation R by the radiation generator 1, the radiation detector 2 accumulates and releases charges and reads signal values to generate a radiographic image corresponding to the dose of received radiation R.

More specifically, when imaging the dynamic state of the specific part P, the radiation detector 2 performs accumulating and releasing charges and reading signal values multiple times in a short period of time (e.g., 15 times per second) to generate a radiographic moving image V consisting of frames $F_1$ to $F_N$.

The radiation detector 2 thus serves as a moving-image generator.

Further, in this embodiment, a radiation entrance surface 2a of the radiation detector 2 can be positioned on the extension of a direction in which the radiation R is emitted with the specific part Pin between, as shown in FIGS. 2, 3A, 3B.

Although the radiation detector 2 shown in FIGS. 2, 3A, 3B is positioned by itself, the radiation detector 2 may be supported by a not-shown imaging stand.

(Dynamic Analysis Apparatus)

The dynamic analysis apparatus 3 consists mainly of a personal computer (PC) or a dedicated apparatus.

The dynamic analysis apparatus 3 analyzes the dynamic state of the specific part P of the subject S on the basis of the radiographic moving image V, which shows the dynamic state of the specific part P.

The dynamic analysis apparatus 3 is described in detail later.

(Console)

The console 4 consists mainly of a PC or a dedicated device.

The console 4 can set various imaging conditions (e.g., tube voltage, tube current, irradiation time (mAs value), parts to be imaged, and imaging directions) for an imaging device in accordance with operations performed by the user or imaging-order information obtained from other systems (e.g., HIS or RIS).

Although the console 4 is separate from the dynamic analysis apparatus 3 in the system 100 in FIG. 1, the console 4 may be integrated with the dynamic analysis apparatus 3.

(Operation of Dynamic Analysis System)

In the system 100 configured as described above, the radiation source 13 of the radiation generator 1 and the radiation detector 2 are positioned to face one another with a certain distance, and the specific part P of the subject S is positioned therebetween. The specific part P is irradiated by the radiation source 13 with radiation R to capture radiographic images of the subject S.

In imaging the subject S in a stationary state, the system 100 emits radiation R and generates a radiographic image only one time in response to one imaging operation (pressing of the irradiation instruction switch). In imaging the dynamic state of the specific part P, the system 100 repeats emitting pulse irradiation and generating a frame $F_1$ to $F_N$ multiple times in a short period of time in response to one imaging operation.

The system 100 sends a moving image generated by the radiation detector 2 to the dynamic analysis apparatus 3, which analyzes the dynamic state of the specific part P shown in the moving image.

(Dynamic State to be Analyzed)

The system 100 can perform analysis using any radiographic moving image V.

The system 100 is, on the other hand, suited for analyzing a radiographic moving image V generated by the radiation detector 2 fixed at a certain position imaging the motion of the specific part P of the subject S.

Examples of the specific part P include bones, joints, and the backbone.

When the specific part P is a bone, the radiographic moving image V shows, for example, rotation of the bone as shown in FIG. 4.

When the specific part P is a joint, the radiographic moving image V shows, for example, extension and flexion, adduction and abduction, and internal and external rotation of the joint as shown in FIG. 5.

In imaging the rotation of the specific part P of the subject S, the system 100 may image the specific part P by rotating the radiation source 13 and the radiation detector 2 to analyze the generated radiographic moving image V showing the relative motion of the specific part P.

<2. Dynamic Analysis Apparatus>

Figure 6:
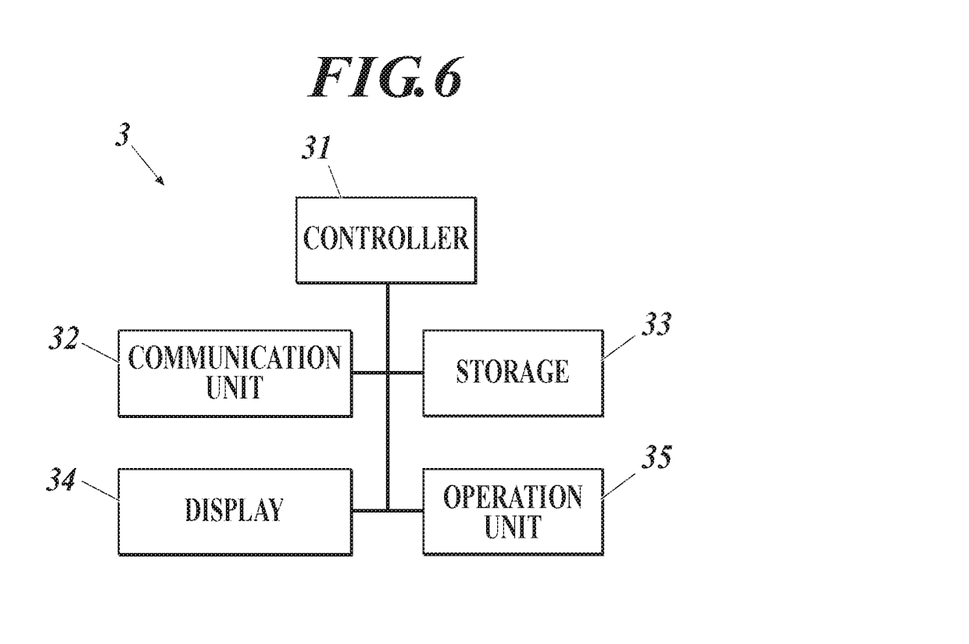
FIG. 6 is a block diagram of a dynamic analysis apparatus included in the dynamic analysis system in FIG. 1.

Next, a detailed configuration of the dynamic analysis apparatus 3 included in the system 100 is described.

Figure 7:
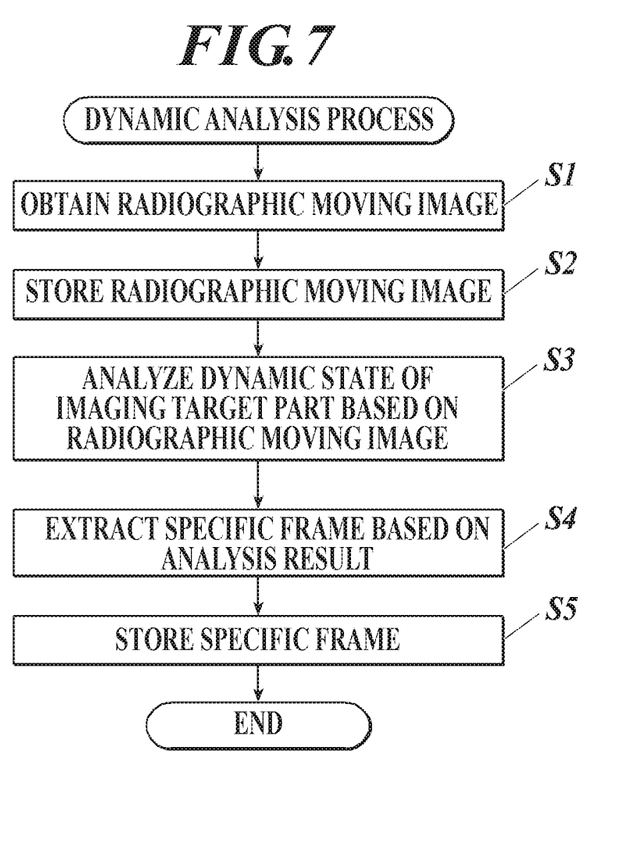
FIG. 7 is a flowchart of a dynamic analysis process that is performed by the dynamic analysis apparatus in FIG. 6.

FIG. 6 is a block diagram of the dynamic analysis apparatus 3. FIG. 7 is a flowchart of a dynamic analysis process that is performed by the dynamic analysis apparatus 3.

(Configuration of Dynamic Analysis Apparatus)

The dynamic analysis apparatus 3 includes a controller 31 (hardware processor), a communication unit 32, and a storage 33, as shown in FIG. 6.

The dynamic analysis apparatus 3 of this embodiment further includes a display 34 and an operation unit 35.

The components 31 to 35 are electrically connected via a bus, for example.

The controller 31 includes a central processing unit (CPU) and a random access memory (RAM).

The CPU of the controller 31 reads various programs stored in the storage 33, loads the read programs into the RAM, executes various processes in accordance with the loaded programs, and thereby centrally controls operation of the components of the dynamic analysis apparatus 3.

The communication unit 32 includes a communication module.

The communication unit 32 sends and receives various kinds of signals and data to and from external devices, such as the radiation detector 2 and the console 4, connected to the communication network N.

The dynamic analysis apparatus 3 may include, instead of the communication unit 32, a reader that reads the content of a storage medium and may import various kinds of data by using the storage medium.

The storage 33 includes a nonvolatile semiconductor memory and/or a hard disk.

The storage 33 stores various programs to be executed by the controller 31 and parameters required for executing the programs. The programs include a program for the dynamic analysis process to be described later.

The storage 33 may also store radiographic images.

The display 34 includes a monitor for displaying images, such as a liquid crystal display (LCD) or a cathode ray tube (CRT).

The display 34 displays various images and so forth in accordance with control signals input by the controller 31.

The operation unit 35 in this embodiment includes: a keyboard including cursor keys, numerical keys, and various function keys; a pointing device, such as a mouse; and a touchscreen superposed on the surface of the display 34.

The operation unit 35 outputs, to the controller 31, control signals corresponding to operations performed by the user.

At least either the display 34 or the operation unit 35 may be shared with the console 4.

(Operation of Dynamic Analysis Apparatus)

The controller 31 of the dynamic analysis apparatus 3, configured as described above, has the following functions.

Analyzing Function

The controller 31 performs, for example, the dynamic analysis process shown in FIG. 7 when a predetermined condition is met.

Examples of the predetermined condition include the following: (i) the dynamic analysis apparatus 3 is turned on, (ii) the dynamic analysis apparatus 3 is connected to the communication network N, (iii) the operation unit receives a certain operation to start the dynamic analysis process, and (iv) the communication unit 32 receives a certain control signal from other devices.

In the dynamic analysis process, the controller 31 firstly performs an obtaining step (Step S1).

In the obtaining step, the controller 31 obtains a radiographic moving image V to be analyzed from other devices.

The controller 31 in this embodiment obtains the radiographic moving image V by receiving data through the communication unit 32.

The controller 31 may obtain the radiographic moving image V by reading data stored in a storage medium.

The controller 31 may start the dynamic analysis process in response to obtaining the radiographic moving image V. In such a case, the obtaining step is unnecessary in the dynamic analysis process.

The controller 31 serves as an obtainer by performing the above-described obtaining step.

After obtaining the radiographic moving image V, the controller 31 in this embodiment performs a storing step (Step S2).

In the storing step, the controller 31 causes the storage 33 to store at least one of the frames $F_1$ to $F_N$, which constitute the captured radiographic moving image V.

The controller 31 in this embodiment causes the storage 33 to store all the frames $F_1$ to $F_N$.

The controller 31 may not perform this storing step and may store the frames $F_1$ to $F_N$ in the second storing step, which is described later.

The controller 31 may not store the radiographic moving image V in the storage 33. Instead, the controller 31 may send the radiographic moving image V to any other device having a storage, such as the console 4 or a not-shown server, and cause the device to store the radiographic moving image V.

After storing the frames $F_1$ to $F_N$, the controller 31 performs an analyzing step (Step S3).

As described above, the controller 31 in this embodiment analyzes (i) the radiographic moving image V generated by imaging the motion of the specific part P of the subject with the radiation detector 2 fixed at a certain position or (ii) the radiographic moving image V generated by imaging relative motion of the specific part P with the radiation detector 2.

In the analyzing step, the controller 31 calculates difference between (i) signal values of pixels constituting the specific part P in one frame among the frames $F_1$ to $F_N$ constituting the radiographic moving image V and (ii) signal values of pixels that are in the frame captured immediately before or after the one frame among the frames $F_1$ to $F_N$ and are at the same coordinates as the pixels constituting the specific part P in the one frame.

The controller 31 serves as an analyzer by performing the above-described analyzing step.

After analyzing the dynamic state of the specific part P, the controller 31 performs an extracting step (Step S4).

In the extracting step, the controller 31 extracts a specific frame $F_S$ among the frames $F_1$ to $F_N$, which constitute the radiographic moving image V, on the basis of the dynamic analysis result in the analyzing step. The specific frame $F_S$ visibly shows the detection target T, which is not shown in the other frames $F_1$ to $F_N$, in the specific part P.

The detection target T is an injured part or a gap part in the specific part P.

Examples of the injured part include a part where bones are incompletely fractured, as shown in FIG. 4.

Examples of the gap part include a gap between the first bone $B_1$ and the second bone $B_2$ of the joint (place where the cartilage exists).

The detection target T transmits more radiation than its surroundings.

In the extracting step, the controller 31 in this embodiment extracts the specific frame $F_S$ on the basis of the calculated difference.

More specifically, the controller 31 determines whether or not the calculated difference exceeds a predetermined threshold for each of the frames $F_1$ to $F_N$.

The detection target T transmits more radiation than its surroundings in imaging, as mentioned above. Further, the signal value of each pixel is proportional to the dose of radiation having penetrated through the subject. According to these, signal values of pixels constituting the detection target T in the specific frame $F_S$ greatly differ from signal values of pixels at the same coordinates in the frame $F_1$ to $F_N$ captured before the specific frame $F_S$. That is, when a frame among the frames $F_1$ to $F_N$ has a difference that exceeds a predetermined threshold, the detection target T is first visible at the timing when the frame is generated. The threshold is set to be a value between signal values of pixels constituting the detection target T and signal values of regions other than the detection target T.

The detection target T may be visible in a plurality of frames among the frames $F_1$ to $F_N$. In other words, one radiographic moving image V may include a plurality of specific frames $F_S$. In such a case, the controller 31 may extract a plurality of specific frames $F_S$.

Further, in the case, the controller 31 may extract a frame(s) among the specific frames $F_S$ that has largest signal values of the pixels constituting the detection target T, namely the frame that shows the detection target T most visibly.

The controller 31 serves as an extractor by performing the above-described extracting step.

The controller 31 in this embodiment performs a second storing step (Step S5) and ends the dynamic analysis process.

In the second storing step, the controller 31 stores (causes the storage 33 to store) at least the specific frame(s) $F_S$ extracted from the frames $F_1$ to $F_N$, which constitute the radiographic moving image V.

Displaying Function

The controller 31 in this embodiment also has a function to cause the display 34 to display the specific frame $F_S$ that is extracted in the dynamic analysis process (extracting step) and that visibly shows the detection target T.

The controller 31 can also highlight the detection target T in displaying.

As the highlighting, the detection target T may be circled, colored, or pointed by an arrow A as shown in FIG. 4, for example.

The controller 31 having the displaying function serves as a displayer.

Instructing Function

The controller 31 in this embodiment also has a function to present conditions for capturing a radiographic image that visibly shows the detection target T, on the basis of the result of analyzing the dynamic analysis obtained in the dynamic analysis process (analyzing step).

The conditions include, for example, the angle of the radiation source 13 and the radiation detector 2 with respect to the detection target T, and the state of the detection target T (e.g., how much the joint is bended).

The controller having the instructing function serves as an instructor.

<3. Advantageous Effects>

The system 100 as described above analyzes the radiographic moving image V captured by imaging the motion of the specific part P of the subject (e.g., rotating, bending and stretching). In other words, the system 100 scans a series of movements of the specific part P. The system 100 then automatically extracts, among the frames $F_1$ to $F_N$ constituting the radiographic moving image V, the specific frame $F_S$ that visibly shows the detection target T of the specific part P that is not shown in the other frames $F_1$ to $F_N$. The system 100 thus can securely detect the detection target T without relying on the imaging skill, as compared with the related art in which a person who perform imaging determines imaging directions and the state of the specific part P (e.g., how much the joint is bended).

Therefore, the system 100 can more easily detect the detection target T in the specific part P, which is visible only when imaged under a certain condition, as compared with the related art.

When the detection target T is a gap between bones, the gap may appear only when the subject moves. It is therefore effective to use the radiographic moving image V, in which the gap is imaged at least any one of the timings, in order to securely detect the detection target T.

<4. Others>

Although the present invention has been described on the basis of the embodiment, the embodiment is not intended to limit the present invention and can be appropriately modified without departing from the scope of the present invention.

For example, although the system 100 in the above embodiment detects an incomplete fraction or a gap between bones as the detection target T, the system 100 can detect any part as the detection target T that is visible only when the specific part P is imaged in a certain direction or in a certain state.

Further, although the dynamic analysis apparatus 3 has the displaying and instructing functions, these functions may belong to the console 4 instead of the dynamic analysis apparatus 3.

As another example, the detection target T may be a region of interest (ROI). For example, the controller 31 obtains positional information of the extracted ROI by performing the above detection process during dynamic imaging. On the basis of the obtained positional information of the ROI, the controller 31 determines whether or not the ROI will be within the image region of a frame image(s) to be captured thereafter. For example, the controller 31 determines whether or not the ROI will be within the image region of a frame image(s) to be captured thereafter on the basis of the obtained positional information of the ROI and the position and the size of the set radiation detector 2. The controller 31 may estimate and determine whether the ROI will be within the image region of a frame image(s) to be captured thereafter on the basis of multiple pieces of positional information having been obtained so far.

When determining that the ROI will be within the image region of a frame image(s) to be captured thereafter, the controller 31 controls the radiation generator 1 to adjust the irradiation field according to the position of the ROI.

For example, the controller 31 controls a collimator of the radiation generator 1 and adjusts the position of the opening of the collimator so that the center of the ROI matches with the center of the irradiation field (irradiation field region) in the frame image to be captured thereafter. According to the size of the ROI, the controller 31 also adjusts (reduces) the size of the opening of the collimator within a range of sizes that allows the ROI to be within the irradiation field in the frame image to be captured.

It is preferable to adjust the position of the opening of the collimator so that the center of the irradiation field matches with the center of the ROI. This is because when, for example, the region outside the irradiation field is removed in each of the captured frame images, the center of the ROI can be fixed among the frame images. Accordingly, an image interpreter can reduce time and effort in interpreting images. Further, the dose to which the examinee is exposed can be reduced by adjusting the size of the opening of the collimator according to the size of the ROI.

When determining that the ROI will not be within the image region of the frame image to be captured thereafter, the controller 31 controls the radiation generator 1 and the radiation detector 2 and adjusts the position of the irradiation field and the position of the radiation detector 2 according to the position of the ROI so that the ROI will be within the irradiation field in the frame image to be captured thereafter. For example, the controller 31 controls the moving mechanism of the radiation detector 2 to move the detector holder, namely the radiation detector 2 so that the center of the frame image to be captured matches with the center of the ROI. The controller 31 also controls the moving mechanism of the radiation generator 1 and/or the collimator to adjust the position of the radiation source and the position of the opening of the collimator so that the center of the irradiation field matches with the center of the ROI in the frame image to be captured. The controller 31 also adjusts the size of the opening of the collimator so that the ROI is within the irradiation field in the frame image.

The positional information of the ROI may be obtained by: capturing an image(s) of the subject during dynamic imaging with a visible-light camera or an infrared camera provided in the vicinity of the collimator; and identifying the ROI in the captured image.

The system 100 is therefore configured as follows.

The system 100 is a dynamic imaging system including an imaging unit that: performs dynamic imaging of a subject with a radiation generator and a radiation detector; and captures multiple frame images showing a dynamic state of the subject. The dynamic imaging system further includes an obtaining unit and an adjusting unit. The obtaining unit obtains positional information of a region of interest (ROI) of the subject during the dynamic imaging performed by the imaging unit. The adjusting unit adjusts an irradiation field of the radiation generator and/or the position of the radiation detector based on the positional information of the ROI of the subject obtained by the obtaining unit.

The obtaining unit may obtain the positional information of the ROI by (i) capturing an image of the subject with the imaging unit, a visible-light camera, or an infrared camera and (ii) identifying the ROI in the captured image.

On the basis of the positional information of the ROI obtained by the obtaining unit, the adjusting unit may determine whether or not the ROI will be within the image region of a frame image(s) to be captured thereafter in the dynamic imaging. When determining that the ROI will not be within the image region of the frame image to be captured, the adjusting unit may adjust the irradiation field and the position of the radiation detector according to the positional information of the ROI.

When determining that the ROI will be within the image region of the frame image to be captured, the adjusting unit may adjust the irradiation field without adjusting the position of the radiation detector.

The adjusting unit may perform the adjustment such that the center of the ROI matches with the center of the irradiation field in the frame image.

Further, as another example, swallowing and/or masticating functions of the subject may be targeted instead of bones and joints as in the above embodiment. However, a dynamic image showing swallowing and/or masticating functions includes various structures, such as bones, soft tissue, contrast media, and metals of artificial teeth. Such a dynamic image needs to be processed so as to improve visibility and to evaluate the functions accurately.

More specifically, when the swallowing function is prioritized in evaluation, it is important that the movements of the hyoid, the epiglottis, and the structures constituting the food-passing channel be mainly observed among the structures relating to feeding and swallowing. In particular, it is important that the movements of the hyoid and the epiglottis be observed. The structures in the dynamic image are classified into three classes: low frequency, medium frequency, and high frequency, based on spatial frequency bands according to predetermined thresholds. The structures of the food-passing channel belong to low frequency, and the hyoid and the epiglottis belong to medium frequency. To exaggerate the frequency components of the hyoid, the epiglottis, and the structures constituting the food-passing channel, in particular to exaggerate the frequency components of the hyoid and the epiglottis, spatial-frequency exaggeration parameters are set so as to exaggerate the low and medium frequency components. The controller 31 then performs frequency resolving processing on each frame image to resolve the frame image into multiple frequency component images having different spatial-frequency bands. In this embodiment, a spatial-frequency filter is used to resolve each frame image into three images of three frequency bands: a low-frequency component image, a medium-frequency component image, and a high-frequency component image. As the spatial-frequency filter, a high-pass filter, a low-pass filter, and a band-pass filter can be used, for example. The controller 31 then exaggerates the frequency components of each frame image. More specifically, the controller 31 multiplies the frequency component images, into which each frame image has been resolved, by the corresponding spatial-frequency exaggeration parameters and adds the multiplied frequency component images to the original frame image.

For example, in the swallowing-function evaluation mode, the controller 31 multiplies the low-frequency component image by a spatial-frequency exaggeration parameter for low-frequency component images, the medium-frequency component image by a spatial-frequency exaggeration parameter for medium-frequency component images, and the high-frequency component image by a spatial-frequency exaggeration parameter for high-frequency component images. The controller 31 then adds these multiplied frequency component images to the original frame image. Accordingly, the low and medium frequency components, in particular the medium-frequency components, are exaggerated. Thus, the image-signal components of the hyoid, the epiglottis, and the structures of the food-passing channels, which need to be focused in evaluating the swallowing function, are exaggerated. In particular, the image-signal components of the hyoid and the epiglottis are exaggerated.

The controller 31 can therefore function as units of an image processing apparatus as described below, in cooperation with a program(s) stored in the storage 33.

The image processing apparatus includes an image obtaining unit and an exaggerating unit. The image obtaining unit obtains a radiographic image of a subject captured through radiography, the subject being in motion of feeding and swallowing. The exaggerating unit exaggerates image signal components of structures relating to feeding and swallowing in the radiographic image.

The exaggerating unit may exaggerate image signal components of a hyoid, an epiglottis, and structures of a food-passing channel, as the structures relating to feeding and swallowing.

The exaggerating unit may exaggerate the image signal components of the structures relating to feeding and swallowing by performing spatial-frequency exaggeration processing on the radiographic image and thereby exaggerating frequency components of spatial frequency bands corresponding to the structures relating to feeding and swallowing.

The exaggerating unit may exaggerate the image signal components of the structures relating to feeding and swallowing by performing the following: (i) resolving the radiographic image into multiple frequency-component images that have different spatial frequency bands, (ii) multiplying a frequency-component image among the frequency-component images having a spatial frequency band corresponding to the structures relating to feeding and swallowing by an exaggeration parameter for exaggerating the frequency-component image, and (iii) combining the multiple frequency-component images and the radiographic image.

The storage 33 may store a program that causes a computer to function as: an image obtaining unit that obtains a radiographic image of a subject captured through radiography, the subject being in motion of feeding and swallowing; and an exaggerating unit that exaggerates image signal components of structures relating to feeding and swallowing in the radiographic image.

Although the above description discloses a hard disk drive and a nonvolatile semiconductor memory as examples of a computer-readable storage medium storing the program according to the present invention, the storage medium is not limited to these. As the computer-readable storage medium, a portable storage medium, such as a CD-ROM, may also be used. Also, as a medium that provides data of the program according to the present invention via a communication line, a carrier wave can be used.

Although embodiments of the present invention have been described and illustrated in detail, the disclosed embodiments are made for purposes of illustration and example only and not limitation. The scope of the present invention includes the scope of the present invention described in the scope of claims and the scope of their equivalents.

What is claimed is:

1. A non-transitory computer-readable storage medium storing a program that causes a computer to perform:
  an obtaining process of obtaining a radiographic moving image showing a motion of a specific part of an examinee;
  an analyzing process of analyzing a dynamic state of the specific part in the radiographic moving image obtained in the obtaining process so as to detect a detection target in frames constituting the radiographic moving image, the detection target being a portion of the specific part that is visible in the radiographic moving image only when the specific part is imaged under a specific condition or in a specific state; and
  an extracting process of extracting, among the frames constituting the radiographic moving image, a specific frame that visibly shows the detection target in the specific part, based on a result of analyzing the dynamic state in the analyzing process.

2. The storage medium according to claim 1, wherein the detection target is an injured part of the specific part or a gap part of the specific part.

3. The storage medium according to claim 1, wherein in the analyzing process, the program causes the computer to calculate a difference between (i) a signal value of a first pixel constituting the specific part in a first frame among the frames constituting the radiographic moving image and (ii) a signal value of a second pixel in a second frame among the frames constituting the radiographic moving image, the second frame being a frame captured immediately before or after the first frame, and the first pixel and the second pixel being at a same coordinate.

4. The storage medium according to claim 3, wherein in the extracting process, the program causes the computer to extract the specific frame based on the calculated difference.

5. The storage medium according to claim 1, wherein the specific part is a bone, a joint, or a backbone.

6. The storage medium according to claim 1, wherein the program causes the computer to distinguish between a frame which visibly shows the detection target and frames which do not visibly show the detection target, from among the frames constituting the radiographic moving image.

7. The storage medium according to claim 6, wherein in the extracting process, the program causes the computer to extract the frame which visibly shows the detection target and to not extract the frame which does not visibly show the detection target, from among the frames constituting the radiographic moving image.

8. The storage medium according to claim 1, wherein the specific condition or the specific state is a specific relative position between a moving image generator which the radiographic moving image is obtained and the specific part.

9. The storage medium according to claim 1, wherein the specific condition or the specific state is a specific imaging direction along which a moving image generator from which the radiographic moving image is obtained images the specific part.

10. A non-transitory computer-readable storage medium storing a program that causes a computer to perform:
  an obtaining process of obtaining a radiographic moving image showing a relative motion of a specific part of an examinee with respect to a moving-image generator;
  an analyzing process of analyzing a dynamic state of the specific part in the radiographic moving image obtained in the obtaining process so as to detect an injured part in frames constituting the radiographic moving image, the injured part being a part of the specific part that is visible in the radiographic moving image only when the specific part is imaged under a specific condition or in a specific state; and
  an extracting process of extracting, among the frames constituting the radiographic moving image, a specific frame that visibly shows the injured part of the specific part, based on a result of analyzing the dynamic state in the analyzing process.

11. A dynamic analysis apparatus comprising a hardware processor configured to execute processes comprising:
   obtaining a radiographic moving image showing a motion of a specific part of an examinee;
   analyzing a dynamic state of the specific part in the obtained radiographic moving image so as to detect a detection target in frames constituting the radiographic moving image, the detection target being a portion of the specific part that is visible in the radiographic moving image only when the specific part is imaged under a specific condition or in a specific state; and
   based on a result of the analyzing, extracting, among the frames constituting the radiographic moving image, a specific frame that visibly shows the detection target in the specific part.

12. A dynamic analysis system, comprising:
   a moving-image generator that generates a radiographic moving image showing a motion of a specific part of an examinee; and
   a hardware processor configured to execute processes comprising:
      analyzing a dynamic state of the specific part in the radiographic moving image generated by the moving-image generator so as to detect a detection target in frames constituting the radiographic moving image, the detection target being a portion of the specific part that is visible in the radiographic moving image only when the specific part is imaged under a specific condition or in a specific state; and
      based on a result of the analyzing, extracting, among the frames constituting the radiographic moving image, a specific frame that visibly shows the detection target in the specific part.

13. The dynamic analysis system according to claim 12, further comprising a storage that stores at least the specific frame extracted by the hardware processor among the frames constituting the radiographic moving image.

14. The dynamic analysis system according to claim 12, wherein the hardware processor is further configured to control display of the extracted specific frame.

15. The dynamic analysis system according to claim 14, wherein the hardware processor is configured to control the display of the extracted specific frame such that the detection target is highlighted therein.

16. The dynamic analysis system according to claim 12, wherein the hardware processor is configured to output information regarding a condition for capturing a radiographic image that visibly shows the detection target therein, based on the result of the analyzing.

* * * * *